United States Patent [19]

Quallich

[11] Patent Number: 5,512,689
[45] Date of Patent: Apr. 30, 1996

[54] PROCESS FOR THE PREPARATION OF INTERMEDIATES IN THE SYNTHESIS OF CHIRAL THIAZOLIDINE-2,4-DIONE DERIVATIVES

[75] Inventor: George J. Quallich, North Stonington, Conn.

[73] Assignee: Pfizer Inc., New York, N.Y.

[21] Appl. No.: 417,502

[22] Filed: Apr. 5, 1995

Related U.S. Application Data

[63] Continuation of Ser. No. 162,028, Dec. 1, 1993, abandoned, which is a continuation of Ser. No. 733,564, filed as PCT/US92/05433, Jul. 1, 1992, abandoned.

[51] Int. Cl.$^6$ .................................................. C07D 263/32
[52] U.S. Cl. .................................................. 548/235
[58] Field of Search .................................................. 548/235

[56] References Cited

U.S. PATENT DOCUMENTS 4,943,635  7/1990  Corey .
5,036,079  9/1991  Clark .

OTHER PUBLICATIONS

Lancaster Catalogue 1991/1992 p. 888.

Quallich et al. Tet. Lett. 34 (5) 785 (1993).

Corey et al., Journal of the American Chemical Society, 1987, 109, 5551–3.

Corey et al., Journal of the American Chemical Society, 1987, 109, 7925–6.

Jones et al., Journal of Organic Chemistry, 1991, 56, 763–9.

Primary Examiner—Robert Gerstl
Attorney, Agent, or Firm—Peter C. Richardson; Gregg C. Benson; Robert T. Ronau

[57] ABSTRACT

A process for the stereoselective preparation of intermediates in the preparation of potent, chiral thiazolidine-2,4-dione hypoglycemics.

9 Claims, No Drawings

PROCESS FOR THE PREPARATION OF INTERMEDIATES IN THE SYNTHESIS OF CHIRAL THIAZOLIDINE-2,4-DIONE DERIVATIVES

This is a continuation of application Ser. No. 08/162,028, filed on Dec. 01, 1993, now abandoned, which is a March 1971 of U.S. Pat. No. 9,205,433 filed Jul. 22, 1992, which is a continuation of Ser. No. 733,564, filed as PCT/US92/05433, Jul. 1, 1992, now abandoned.

BACKGROUND OF THE INVENTION

The compound of formula I, depicted below, has been reported by Clark, International Patent Publication WO 89/08651 (now U.S. Pat. No. 5,036,079), to be a potent hypoglycemic in mammals.

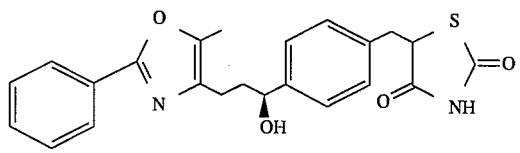

A key intermediate in the synthesis of this compound is the compound of formula II, depicted below, which has a bromo atom poised for conversion into the thiazolidinylmethyl moiety of the final product.

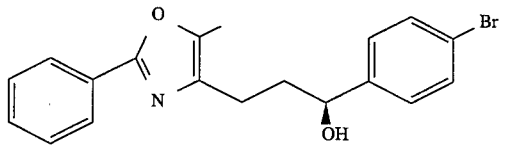

This compound has previously been prepared by reduction of the precursor ketone of formula III and subsequent diastereomeric resolution of the racemic alcohol as reported by Clark (vide supra). This resolution, while

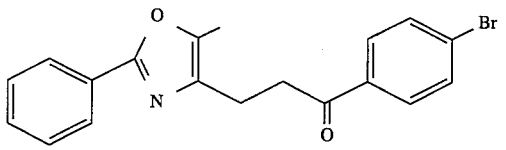

generally affording a high degree of optical purity, is a time-consuming, two-step process which, even under the best of circumstances, gives only a 50% yield of the desired product from the starting ketone.

The process of the present invention solves this problem by performing the reduction of the ketone under conditions which generate alcohol (II) in optically pure form. The process also lends itself to preparation of the corresponding (R) enantiomer, likewise in optically pure form.

The stereoselective reduction process of this invention involves the use of a borane reducing agent and a chiral oxazaborolidine catalyst. Corey, et al. (Journal of the American Chemical Society, 1987, 109, 5551–3 and 7925–6) have described generally the reduction of a limited number of ketones with boranes utilizing chiral oxazaborolidines to elicit enantioselectivity. However, recent studies by Jones, et al. (Journal of Organic Chemistry, 1991, 56, 763–9) have demonstrated that the method loses its effectiveness when molecules possessing borane coordination sites are present in the reaction mixture. Examples of compounds containing borane coordination sites include but are not limited to such compounds as boronic acids, boroxines, prolinols, amines, thiazoles and oxazoles. This loss of effectiveness is manifested in diminished enantioselectivity. The present invention is directed to a process in which the deleterious effect of said borane coordination sites has been overcome.

SUMMARY OF THE INVENTION

The present invention is directed to a process for the stereoselective preparation of a compound of formula IV,

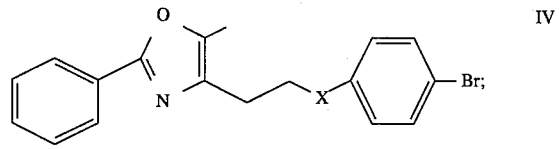

wherein X is

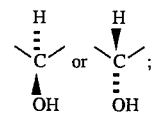

and said compound is substantially free of its corresponding enantiomeric form. The process involves stereoselective reduction of a ketone of formula III. Said ketone is reduced with about 2 to 3 molar equivalents of a borane reducing agent such as borane methyl sulfide complex, catecholborane or borane tetrahydrofuran, in the presence of a chiral oxazaborolidine catalyst of formula V,

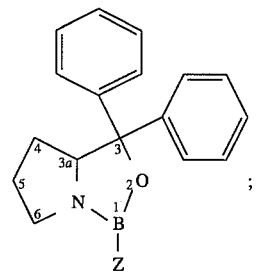

wherein the stereochemical configuration at the 3a carbon is R, or S; and Z is $(C_1-C_4)$alkyl, phenyl or $(C_7-C_8)$phenylalkyl. When the configuration at said 3a carbon is R, the resulting compound of formula IV has the S configuration wherein X is

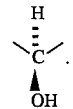

When the configuration at said 3a carbon is S, the resulting compound of formula IV has the R configuration wherein X is

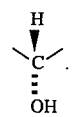

The reduction is carried out in a cyclic ether solvent such as dioxane or tetrahydrofuran at a temperature of about −20° C. to +40° C.

DETAILED DESCRIPTION OF THE INVENTION

The present invention, directed to a process for the stereoselective preparation of a compound of formula IV, depicted above, is readily carried out. The ketone reactant of formula III is prepared by literature methods (Clark, vide supra). Said ketone is reacted with a borane reducing agent such as borane methyl sulfide complex, catacholborane or borane tetrahydrofuran. Most preferred is borane methyl sulfide complex. To obtain the desired results, about 2 to 3 equivalents of said reducing agent are required. The reaction is carried out in a cyclic ether solvent such as dioxane or tetrahydrofuran, with tetrahydrofuran being more preferred, and at a temperature range of from about −20° C. to +40° C. The reaction is usually carried out at ambient temperature, with the term "ambient temperature" being defined as the temperature of the room within which the reaction is being carried out when that temperature is in the range of about +18° C. to +25° C.

To elicit the enantioselectivity which is desired, the reaction is run in the presence of a chiral oxazaborolidine catalyst of formula V, depicted above, wherein the stereochemical configuration at the 3a carbon is either R or S; and Z is $(C_1-C_4)$alkyl, phenyl or $(C_7-C_9)$phenylalkyl. More preferred is the case wherein Z is methyl, n-butyl or phenyl. Most preferred is the case where Z is methyl. When an S configuration at the hydroxyl carbon of the product is required, as in formula II, the configuration of the 3a atom in the oxazaborolidine catalyst of formula V must be R. Thus, to prepare the compound of formula II, the most preferred catalyst is (R)-tetrahydro-1-methyl-3,3-diphenyl-1H,3H-pyrrolo[1,2-c][1,3,2]oxazaborole.

When the R configuration at the hydroxyl carbon of the product is required, affording the enantiomer of the compound of formula Ii, the configuration of the 3a atom in the catalyst of formula V must be S. Thus, to prepare the R enantiomer of formula VI, the most preferred

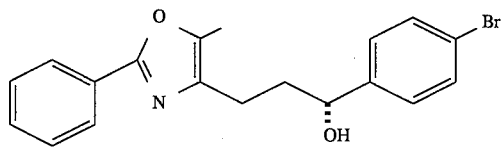

VI catalystis(S)-tetrahydro-1-methyl-3,3-diphenyl-1H,3H-pyrrolo[1,2-c][1,3,2]oxazaborole.

The intermediate of formula II is elaborated to the potent hypoglycemic of formula I in the straightforward manner reported by Clark (vide supra). Said intermediate is also useful in preparing various ether derivatives of these hypoglycemics. Thus, said intermediate of formula II is reacted with sodium hydride and a halide of the formula RX; wherein X is Br, I or Cl; and R is $(C_1-C_4)$alkyl or alkoxyalkyl of the formula $(CH_2)_pO(CH_2)_mCH_3$; wherein p=2, 3 or 4 and m=0, 1, 2 or 3. The reaction is carried out in a reaction inert solvent at a temperature of about, 0° C. to 200° C. The term 'reaction inert solvent' is meant to define a solvent which does not prevent the normal course of reaction from occurring, such as tetrahydrofuran, dimethoxyethane, diethyl ether or dioxane. Most preferred is tetrahydrofuran. The temperature of the reaction is conveniently the reflux temperature of the reaction mixture. The ethers prepared in this manner are elaborated to the ether derivatives of the alcohol of formula I as taught by Clark (vide supra), with the only exception being that deprotection of the silyl ether to the alcohol is no longer required.

The R alcohol (formula VI) may be converted to the corresponding R ethers via a similar process.

The present invention is further illustrated by the following examples. However, it should be understood that the invention is not limited to the specific details of these examples. All reactions are carried out under an inert atmosphere, such as nitrogen, unless otherwise specified. All solvents are pre-dried or purchased in a dry form. Nomenclature used herein is based on Rigaudy and Klesney, IUPAC Nomenclature of Organic Chemistry, 1979 Ed., Pergamon Press, New York, New York, 1979.

EXAMPLE 1

(S)-4-[3-(5-Methyl-2-phenyl-4-oxazolyl)-1-hydroxypropyl]bromobenzene

4-[3-(5-Methyl-2-phenyl-4-oxazolyl)propionyl]bromobenzene (20 g, 54 mmol) was dissolved in THF (200 mL) at ambient temperature and treated with 4A molecular sieves (10 g, predried under high vacuum at 150° C. overnight). After standing overnight, the solution was decanted from the sieves and was found to have 0.0092% water (by Karl Fisher analysis). (R)-Tetrahydro-1-methyl-3,3-diphenyl-1H,3H-pyrrolo[1,2-c][1,3,2]oxazaborole (748 mg, 2.7 mmol) was added at ambient temperature and the solution was treated with borane methyl sulfide complex (2M in THF, 78 mL, 152 mmol) dropwise over 75 minutes. The reaction mixture was stirred for an additional 15 minutes, cooled to 0° C. and quenched by the dropwise addition of methanol (280 mL). The quenched solution was stirred for 18 hours at ambient temperature. The solvents were removed in vacuo and the residue was dissolved in methylene chloride (200 mL) and washed successively with pH 4 aqueous phosphate buffer (200 mL), water (200 mL) and dried (MgSO$_4$). The organic layer was distilled at atmospheric pressure until a volume of 100 mL remained. Hexane was added, and the distillation was continued until the temperature of the distillate reached 62° C. The heat source was removed, and the residue crystallized and granulated over 16 hours. A white solid was collected by vacuum filtration and was dried under high vacuum to afford the title compound (17.46 g, 87%, >99% enantiomeric excess).

EXAMPLE 2

(R)-4-[3-(5-Methyl-2-phenyl-4-oxazolyl)-3-hydroxypropyl]bromobenzene

4-[3-(5-Methyl-2-phenyl-4-oxazolyl)-3-hydroxypropyl]bromobenzene (20.0 g, 54 mmol) was dissolved in THF (200 mL). Borane methyl sulfide complex (2M in THF, 76 mL, 152 mmol) was diluted in THF (124 mL). These two solutions were added separately and simultaneously over 105 minutes to (S)-Tetrahydro-1,3,3-triphenyl-1H,3H-pyrrolo[1,2-c][1,3,2]oxazaborole (920 mg, 2.71 mmol) in THF (20 mL) at ambient temperature. The reaction mixture was stirred an additional 105 minutes after addition was complete, then cooled to 0° C. and quenched reaction mixture was stirred for 16 hours, at which time the solvents were removed in vacuo and the residue was dissolved in methylene chloride, (200 mL) water (200 mL) and dried (MgSO$_4$). The solvent was removed in vacuo to yield a thick oil (20.39 g, 100%, 84% ee).

EXAMPLE 3

(S)-5-[4-(3-(5-Methyl-2-phenyl-4-oxazolyl)-1-hydroxypropyl)benzyl]thiazolidine-2,4-dione The sodium salt of (S)-5-[4-(3-(5-Methyl-2-phenyl-4-oxazolyl)-1-propionyl)benzyl]thiazolidine-2,4-dione (1.19 g, 2.69 mmol) was dissolved in THF (17 mL) and treated with t-butyldimethylsilyl trifluoromethanesulfonate (0.62 mL, 2.69 mmol) and the reaction mixture was stirred for 30 minutes at ambient temperature. (R)-Tetrahydro-1-methyl-3,3-diphenyl-1H,3H-pyrrolo[1,2-c][1,3,2]oxazaborole 0.074 g, 0.267 mmol) was added, followed by dropwise addition of borane methyl sulfide complex (2M in THF, 4,97 mL, 9.94 mmol) over 2.5 hours. The reaction mixture was stirred at ambient temperature for an additional two hours, cooled to 0° C., and quenched by the dropwise addition of methanol (30 mL). The quenched solution was stirred for 16 hours, at which time the solvents were removed in vacuo and the residue was dissolved in methylene chloride, washed with pH 4 aqueous phosphate buffer (40 mL), water (40 mL) and dried (MgSO$_4$). The solvent was removed in vacuo and the residue was purified on silica gel, eluting with hexane/ethyl acetate (1/1), to afford the title compound of example three (0.907 g, 80%, 75% ee) as a white foam.

EXAMPLE 4

(S)-4-[1-(t-butyldimethylsilyloxy)-3-(5-methyl-2-phenyl)-4-oxazolyl)propyl]bromobenzene The title compound of Example 1 (769 mg, 2.0 mmol), t-butyldimethylsilylchloride (377 mg, 2.5 mmol) and imidazole (340 mg, 5.0 mmol) were combined in DMF (10 mL) and stirred at room temperature for 24 hours. The reaction mixture was diluted with water (100 mL) and extracted with ethyl acetate (2×100 mL). The organic layers were combined, washed with water (100 mL), saturated aqueous sodium bicarbonate (100 mL), brine (100 mL) and dried (MgSO$_4$). The solvent was removed in vacuo to afford the title compound as a gum (860 mg, 85%). $^1$HNMR (60 MHz, CDCl$_3$): δ 0.5 (d, 6H), 1.0 (s, 9H), 2.0–2.7 (m, 4H), 2.3 (s, 3H), 4.8 (t, J=5 Hz, 1H), 7.1–7.6 (m, 7H), 7.9–8.1 (m, 2H).

EXAMPLE 5

(S)-4-[1-(t-butyldimethylsilyloxy)-3-(5-Methyl-2-phenyl-4-oxazolyl)propyl]benzaldehyde n-Butyllithium (1.6M in hexane, 1.3 mL) was added over ten minutes to a cooled (−78° C.) solution of the title compound of Example 4 (780 mg, 1.6 mmol) in THF (60 mL). The reaction mixture was stirred at −78° C. for an additional 50 minutes and dry DMF (152 mg, 2.0 mmol) was added. The reaction mixture was stirred for an additional 1.5 hours at −78° C. and then at room temperature for 1.5 hours. The reaction mixture was diluted with ethyl acetate (200 mL) and washed with water (50 mL), 10% aqueous saturated sodium bicarbonate (50 mL), water (50 mL), brine (50 mL) and dried (MgSO$_4$). The solvent was removed in vacuo and the residue was purified on silica gel, eluting with hexane/diethyl ether (4/1), to afford the title aldehyde (650 mg, 93%). $^1$HNMR (60 MHz, CDCl$_3$): δ0.5 (d, 6H), 1.0 (s, 9H), 2.0–2.7 (m, 4H), 2.3 (s, 3H), 4.9 (dd, J=6 Hz, 12 Hz, 1H), 7.2–8.0 (m, 9H), 10.1 (s, 1H).

EXAMPLE 6

(S)-5-[4-(1-t-butylidimethylsilyloxy)-3-(5-methyl-2-phenyl-4-oxazolyl)propyl)phenyl]methylene]thiazolidine -2,4-dione The title compound of Example 5 (341 mg, 0.78 mmol), 2,4-thiazolidinedione (183 mg, 1.56 mmol) and piperidine (14 mg, 0.15 mmol) were combined in ethanol (10 mL) and refluxed for 18 hours. The reaction mixture was cooled to room temperature and concentrated in vacuo. The residue was purified on silica gel, eluting with hexane/ethyl acetate/acetic acid (16/4/1), to afford a solid which was triturated in hexane to yield the title compound as a white solid (163 mg, 39%). mp 158°–160° C. $^1$HNMR (300 MHz, CDCl$_3$): δ–0.5 (d, 6H), 1.0 (s, 9H), 2.0–2.7 (m, 4H), 2.3 (s, 3H), 4.9 (m, 1H), 7.6–7.7 (m, 7H), 7.8 (s, 1H), 8.0 (m, 2H).

EXAMPLE 7

(S)-5-[4-(1-(t-butyldimethylsilyloxy)-3-(5-methyl-2-phenyl-4-oxazolyl)propyl)benzyl]thiazolidine-2,4-dione The title compound of Example 6 (160 mg, 0.3 mmol) and 10% palladium on carbon (160 mg) were combined in THF (10 mL) and hydrogenated on a Parr Shaker at 50 PSI and room temperature for 22 hours. The suspension was filtered through diatomaceous earth and the solvent was removed in vacuo to afford the title compound as a gum (180 mg, %). $^1$HNMR (300 MHz, CDCl$_3$): δ0.5 (d, 6H), 1.0 (s, 9H), 2.0–2.2 (m, 2H), 2.3 (s, 3H), 2.4–2.6 (m, 2H), 3.4 (dd, 1H), 4.3 (dd, 1H), 4.7 (dd, 1H), 7.0–7.3 (m, 7H), 7.8 (m, 2H).

EXAMPLE 8

Sodium Salt of (S)-5-[4-(3-(5-methyl-2-phenyl-4-oxazolyl)-1-hydroxypropyl)benzyl]thiazolidine-2,4-dione The title compound of Example 7 (160 mg, 0.3 mmol) was dissolved in THF (5 mL) and treated with 3.5% aqueous perchloric acid (3 mL). The reaction mixture was stirred at room temperature for 12 hours, diluted with ethyl acetate (25 mL), washed with water (25 mL), brine (25 mL) and dried (MgSO$_4$). The solvent was removed in vacuo and the residue was purified on silica gel, eluting with hexane/ethyl acetate/acetic acid (66/33/1), to afford 115 mg of the free base as a gum. The gum was dissolved in methanol (10 mL), treated with sodium methoxide (15 mg, 0.3 mmol) and stirred at room temperature for 2.5 hours. The solvent was removed in vacuo and the residue was triturated with diethyl ether to afford the title compound as a solid (79 mg, 60%). mp 235°–240° C. $^1$HNMR (300 MHz, DMSO-d$_6$): δ1.9 (m, 2H), 2.3 (s, 3H), 2.5 (m, 2H), 2.7 (dd, 1H), 3.4 (dd, 1H), 4.1 (dd, 1H), 4.5 (m, 1H), 5.2 (d, 1H, hydroxyl proton), 7.1 (d, 2H), 7.5 (m, 3H), 7.9 (m, 2H).

EXAMPLE 9

(S)-4-[3-(5-methyl-2-phenyl-4-oxazolyl)-1-ethoxypropyl]bromobenzene

The title compound of Example 1 (1.0 g, 2.7 mmol) and sodium hydride (324 mg, 6.7 mmol) were dissolved in THF (30 mL) at 0° C. The reaction mixture was treated with ethyl iodide (1.0 g, 6.7 mmol) and the contents were refluxed for 18 hours. The reaction mixture was cooled to room temperature and concentrated in vacuo, dissolved in water (25 mL) and extracted twice with ethyl acetate (50 mL). The organic extracts were combined, washed with water (25 mL), brine (25 mL) and dried (MgSO$_4$). The solvent was removed in vacuo and the residue was purified on silica gel, eluting with hexane/ethyl acetate (3/1), to afford the title compound as a gum (1.1 g, 90%). $^1$HNMR (300 MHz, CDCl$_3$): δ1.15 (t, 3H), 2.0 (m, 2H), 2.3 (s, 3H), 2.5 (t, 2H), 3.2–3.4 (m, 2H), 4.2 (dd, 1H), 7.2 (d, 2H), 7.4 (m, 5H), 7.9 (d, 2H).

EXAMPLE 10

The following optically pure ether derivatives were prepared by reaction of the appropriate alkyl halide (RX) with the requisite optically pure alcohol of the indicated stereochemistry using substantially the same procedure recited in Example 9.

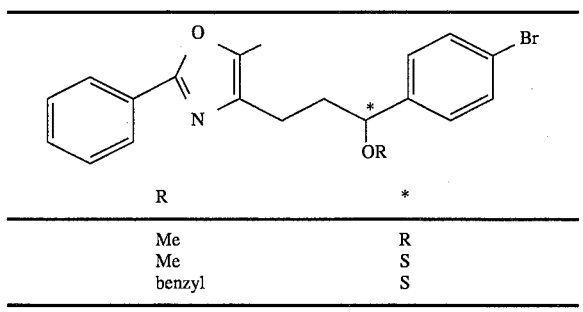

| R | * |
|---|---|
| Me | R |
| Me | S |
| benzyl | S |

I claim:

1. A process for the stereoselective preparation of a compound of formula VI,

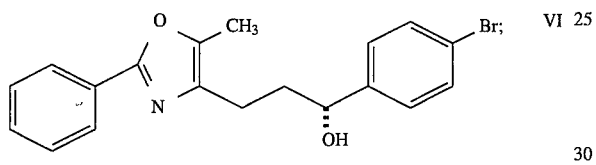

said compound being essentially free of its enantiomeric form; and said process comprising treating a ketone of formula III,

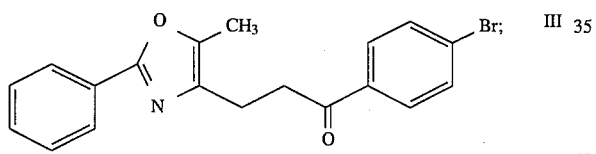

with about 2 to 3 molar equivalents of a borane reducing agent selected from the group consisting of borane methyl sulfide complex, catecholborane and borane tetrahydrofuran, said treatment being conducted in the presence of a chiral oxazaborolidine catalyst of the formula VII,

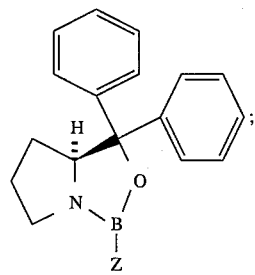

wherein Z is $(C_1-C_4)$alkyl, phenyl or $(C_7-C_9)$phenylalkyl, in a cyclic ether solvent at a temperature of about $-20°$ C. to $+40°$ C.

2. A process for the stereoselective preparation of a compound of formula II,

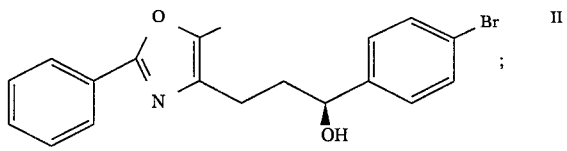

said compound being essentially free of its enantiomeric form; and said process comprising treating a ketone of formula III,

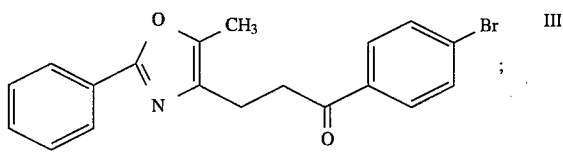

with about 2 to 3 molar equivalents of a borane reducing agent selected from the group consisting of borane methyl sulfide complex, catecholborane and borane tetrahydrofuran, said treatment being conducted in the presence of a chiral oxazaborolidine catalyst of formula VIII,

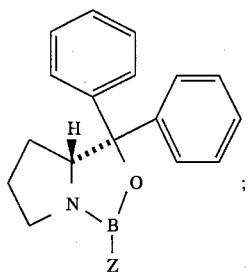

wherein Z is $(C_1-C_4)$alkyl, phenyl or $(C_7-C_9)$phenylalkyl, in a cyclic ether solvent at a temperature of about $-20°$ C. to $+40°$ C.

3. The process according to claim 1 wherein said cyclic ether solvent is tetrahydrofuran and Z is methyl, n-butyl or phenyl.

4. The process according to claim 2 wherein said cyclic ether solvent is tetrahydrofuran and Z is methyl, n-butyl or phenyl.

5. The process according to claim 3 wherein said borane reducing agent is borane methyl sulfide complex.

6. The process according to claim 5 wherein Z is methyl.

7. The process according to claim 4 wherein said borane reducing agent is borane methyl sulfide complex.

8. The process according to claim 7 wherein Z is methyl.

9. The process according to claim 7 wherein Z is phenyl.

* * * * *